(12) United States Patent
Furumai et al.

(10) Patent No.: US 10,072,320 B2
(45) Date of Patent: Sep. 11, 2018

(54) METHOD OF PRODUCING STEEL MATERIAL

(71) Applicant: JFE STEEL CORPORATION, Tokyo (JP)

(72) Inventors: Kohei Furumai, Tokyo (JP); Norichika Aramaki, Tokyo (JP); Yuji Miki, Tokyo (JP); Takeshi Murai, Tokyo (JP); Toru Inoue, Tokyo (JP); Yukio Usui, Tokyo (JP); Tomoharu Ishida, Tokyo (JP)

(73) Assignee: JFE Steel Corporation, Tokyo (JP)

( * ) Notice: Subject to any disclaimer, the term of this patent is extended or adjusted under 35 U.S.C. 154(b) by 440 days.

(21) Appl. No.: 14/903,103

(22) PCT Filed: Jun. 4, 2014

(86) PCT No.: PCT/JP2014/064812
§ 371 (c)(1),
(2) Date: Jan. 6, 2016

(87) PCT Pub. No.: WO2015/005023
PCT Pub. Date: Jan. 15, 2015

(65) Prior Publication Data
US 2016/0145718 A1  May 26, 2016

(30) Foreign Application Priority Data
Jul. 10, 2013 (JP) .................................. 2013-144370

(51) Int. Cl.
*C22C 1/06* (2006.01)
*C21C 7/04* (2006.01)
(Continued)

(52) U.S. Cl.
CPC .................. *C22C 1/06* (2013.01); *C21C 7/04* (2013.01); *C21C 7/10* (2013.01); *C22C 1/02* (2013.01);
(Continued)

(58) Field of Classification Search
CPC .. C22C 1/06; C22C 33/00; C21C 7/04; C21C 7/10; C21C 1/02; G01N 21/67; G01N 21/69
See application file for complete search history.

(56) References Cited

U.S. PATENT DOCUMENTS

2006/0016520 A1  1/2006  Numata

FOREIGN PATENT DOCUMENTS

CN    1989263    6/2007
CN    101565771   10/2009
(Continued)

OTHER PUBLICATIONS

Chinese Office Action with partial English language translation for Application No. 2014800388994, dated Feb. 20, 2017, 8 pages.
(Continued)

*Primary Examiner* — Jennifer A Smith
*Assistant Examiner* — Alexandra Marie Moore
(74) *Attorney, Agent, or Firm* — RatnerPrestia

(57) ABSTRACT

A method of producing a steel material includes a step of adding Ca to molten steel with an amount of Ca adjusted within a range satisfying the formula (1) below:

$$0.5 \leq \frac{\{Ca \cdot y/100 - ([S \cdot W/100] \cdot 40.08/32.07]\frac{56.08}{40.08}}{([Al_2O_3] \cdot W/100)} \leq 1.5 \quad (1)$$

(Continued)

where Ca is the amount [kg] of Ca added, y is an yield [%] of Ca, [S] is a concentration [% by mass] of S in the steel before addition of Ca, [Al$_2$O$_3$] is an amount [% by mass] of Al$_2$O$_3$ in the steel before addition of Ca, and W is a weight [kg] of the molten steel.

4 Claims, 4 Drawing Sheets

(51) Int. Cl.
    *G01N 21/67* (2006.01)
    *C21C 7/10* (2006.01)
    *C22C 1/02* (2006.01)
    *G01N 21/69* (2006.01)

(52) U.S. Cl.
    CPC .............. *G01N 21/67* (2013.01); *G01N 21/69* (2013.01); *G01N 2021/695* (2013.01)

(56) References Cited

FOREIGN PATENT DOCUMENTS

| | | |
|---|---|---|
| JP | 0199761 | 4/1989 |
| JP | 08029349 | 2/1996 |
| JP | 08053707 | 2/1996 |
| JP | 08333619 | 12/1996 |
| JP | 10001124 | 1/1998 |
| JP | 10121124 A | 5/1998 |
| JP | 2001214237 | 8/2001 |
| JP | 2004238707 A | 8/2004 |
| JP | 2004344891 | 12/2004 |
| JP | 201189180 | 5/2011 |
| JP | 2012026745 A | 2/2012 |
| TW | 325500 | 1/1998 |

OTHER PUBLICATIONS

Korean Office Action with partial English language translation for Application No. 10-2015-7035763, dated Feb. 25, 2017, 5 pages.
Taiwanese Office Action for Taiwanese Application No. 103123545, dated Oct. 26, 2016, with Concise Statement of Search Report, 6 pages.
Chinese Office Action with English language Search Report for 201480038899.4, dated Sep. 2, 2016, 7 pages.
Supplementary European Search Report for Application No. 14822459.5, dated Feb. 21, 2017, 9 pages.
Effect of Calcium on the Quality of Tube Rounds and Seamless Tubes, E. L. Zats et al., Metallurgist, Springer New York LLC, vol. 25, No. 3-4, pp. 94-96, Mar. 1, 1981, 3 pages.
International Search Report for International Application No. PCT/JP2014/064812 dated Sep. 2, 2014.
Korean Office Action for Application No. 10-2015-7035763 with Concise Statement of Relevance, dated Jul. 27, 2016, 5 pages.

METHOD OF PRODUCING STEEL MATERIAL

CROSS REFERENCE TO RELATED APPLICATIONS

This is the U.S. National Phase application of PCT/JP2014/064812, filed Jun. 4, 2014, which claims priority to Japanese Patent Application No. 2013-144370, filed Jul. 10, 2013, the disclosures of each of these applications being incorporated herein by reference in their entireties for all purposes.

TECHNICAL FIELD OF THE INVENTION

The present invention relates to a method of producing a steel material having high HIC resistance, the method including adding Ca to molten steel contained in a container to control the components of the molten steel.

BACKGROUND OF THE INVENTION

In a steel material, such as a line pipe, which needs to have hydrogen induced cracking resistance, addition of Ca so as to cause Ca to react with S in the steel to form CaS is effective at making MnS that causes hydrogen induced cracking harmless. However, when Ca is added, the added Ca reacts with $Al_2O_3$, which is a deoxidation product, and $CaO$—$Al_2O_3$ inclusions are thereby generated. If the amount of Ca is insufficient, some part of S in the steel remains unreacted, causing generation of MnS. If the amount of Ca is excessively large, oxide with high CaO content is generated. Both the above MnS and oxide cause deterioration of hydrogen induced cracking resistance. Therefore, to improve the hydrogen induced cracking resistance, it is advantageous to add Ca such that the composition of the inclusions is controlled appropriately.

If the amount of Ca added is excessively large, CaO inclusions may cause HIC (Hydrogen Induced Cracking) to occur. Therefore, in aluminum killed steel, it is advantageous that the required amount of Ca be added according to the amount of $Al_2O_3$ present in molten steel before addition of Ca to thereby control the composition of the inclusions so that the inclusions are made harmless. Patent Literature 1 discloses a method of optimally controlling the amount of Ca added. In this method, after completion of secondary refining, the total oxygen content (T.[O]) in molten steel is analyzed, and Ca is added to the molten steel in an amount determined on the basis of the analysis results immediately before the start of pouring of the molten steel into a tundish.

PATENT LITERATURE

Patent Literature 1: Japanese Patent Application Laid-open No. 2011-89180

SUMMARY

However, the method described in Patent Literature 1 has a problem in that the composition of the inclusions cannot be controlled because of variations in the yield of Ca.

The present invention has been made to solve the foregoing problem, and it is an object to provide a steel material production method that can produce a steel material having high HIC resistance.

The present inventors have found that the composition of the inclusions can be controlled by adding Ca according to the amount of $Al_2O_3$ present after completion of secondary refining. The present inventors have also found that, by adjusting the amount of Ca added such that the amount satisfies the formula (1) described later, the composition of the inclusions can be controlled such that the occurrence of hydrogen induced cracking can be reduced, and this allows a steel material having high HIC resistance to be produced.

A method of producing a steel material according to an embodiment of the present invention based on the above-described findings includes a step of adding Ca to molten steel with an amount of Ca adjusted within a range satisfying the formula (1) below:

$$0.5 \leq \frac{\{Ca \cdot y/100 - ([S] \cdot W/100) \cdot 40.08/32.07\}\frac{56.08}{40.08}}{([Al_2O_3] \cdot W/100)} \leq 1.5 \quad (1)$$

where Ca is the amount [kg] of Ca added,
y is an yield [%] of Ca,
[S] is a concentration [% by mass] of S in the steel before addition of Ca,
$[Al_2O_3]$ is an amount [% by mass] of $Al_2O_3$ in the steel before addition of Ca, and
W is a weight [kg] of the molten steel.

Moreover, the method of producing a steel material according to an embodiment of the present invention further includes a step of analyzing, after secondary refining, the amount of $Al_2O_3$ in the molten steel, and thereafter adding CaSi to the molten steel in a ladle.

Moreover, in an embodiment of the above-described invention, the method of producing a steel material produces the steel material with the amount of $Al_2O_3$ in the molten steel analyzed by spark discharge atomic emission spectroscopy, and the method further includes an intensity ratio computing step of determining aluminum/iron light emission intensity ratios of a plurality of discharge pulses, an alumina fraction computing step of computing an alumina fraction determined using the formula (2) below, a step of arranging the light emission intensity ratios of the respective discharge pulses obtained in the intensity ratio computing step in ascending order, using a light emission intensity ratio at a certain position equal to or lower than 30% of the total number of discharge pulses as a representative aluminum intensity ratio, and then computing an alumina intensity ratio (=the alumina fraction×a representative aluminum intensity ratio) using a product of the alumina fraction computed in the alumina fraction computing step and the representative aluminum intensity ratio, and a quantitative step of computing the amount of alumina (in the steel) using a relational formula between the alumina intensity ratio and the amount of alumina (in the steel) determined by chemical analysis:

Alumina fraction=Number of discharge pulses with
Al/Fe intensity ratio larger than threshold value
α/total number of pulses  (2)

where the threshold value α is determined using a frequency distribution diagram having a horizontal axis representing the light emission intensity ratios for the discharge pulses and a vertical axis representing frequency, the threshold value α being a value obtained by multiplying a mode of the light emission intensity ratios by a factor of $f_1$ ($1.5 \leq f_1 \leq 2.5$).

According to the present invention, a steel material having high HIC resistance can be produced.

DETAILED DESCRIPTION OF EMBODIMENTS OF THE INVENTION

Figure 1:
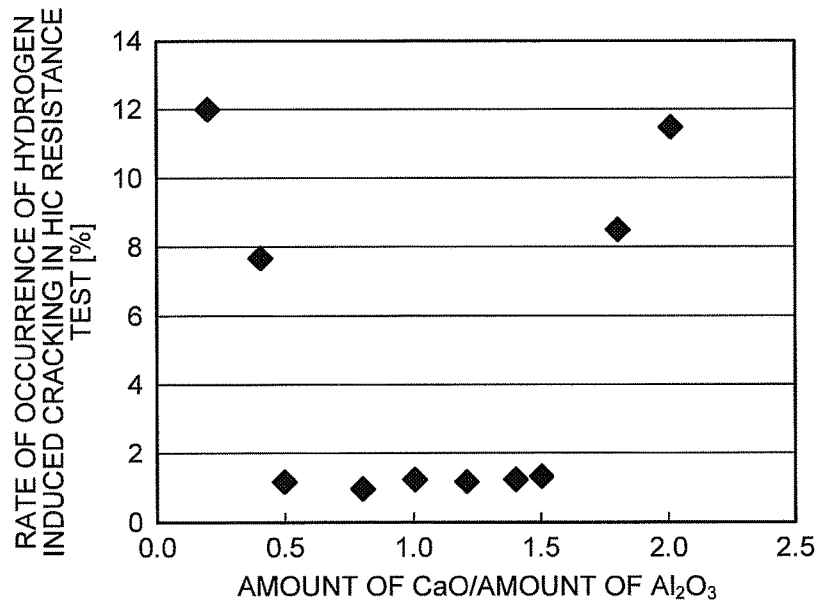
FIG. 1 is a graph showing the relation between the rate (%) of occurrence of hydrogen induced cracking in an HIC resistance test and the amount of CaO/the amount of $Al_2O_3$ in molten steel.

One embodiment of the present invention will next be described in detail with reference to the drawings. However, the present invention is not limited to the embodiment.

The process to arrive at the present invention will next be described. First, the relation between the composition of inclusions in a slab and the rate of occurrence of hydrogen induced cracking was examined. The composition of inclusions in an area of 100 mm² in the slab was analyzed using particle analysis SEM (scanning electron microscopy). In the particle analysis SEM that is recently becoming widespread, information about the composition of inclusions, information about the size thereof, and information about the number thereof can be acquired simultaneously, and the composition of the inclusions analyzed by the particle analysis SEM is highly suitable as an indicator of HIC resistance in the present invention.

From the results of the analysis by the particle analysis SEM, it was found that many of the inclusions were composite inclusions of $CaO$—$Al_2O_3$. In addition, the results of evaluation of the average composition of the inclusion particles and the rate of occurrence of hydrogen induced cracking showed that, when the ratio of CaO to $Al_2O_3$ in the composite inclusions was 1 ($CaO/Al_2O_3 \cong 1$), the HIC resistance was high. Specifically, when CaO and $Al_2O_3$ are combined at a composition ratio of 1:1, it is considered that a reduction in the melting point of the inclusions and a floatation separation effect due to aggregation of the inclusions can be expected as the properties of the composite inclusions, so that good correlation with the HIC resistance can be obtained.

When a wire filled with a CaSi alloy or a powdery Ca alloy is added to molten steel that has been deoxidized in secondary refining, Ca and $Al_2O_3$ in the molten steel react with each other to generate $CaO$—$Al_2O_3$ inclusions. Therefore, the composition of the inclusions can be controlled by analyzing the amount of $Al_2O_3$ after completion of RH and then adding Ca according to the amount of $Al_2O_3$.

The amount of CaO in the molten steel can be determined by using the amount of Ca added with the yield of Ca taken into consideration and the amount of [S] before addition of Ca, i.e., by subtracting the amount of Ca reacted with S in the molten steel from the amount of Ca added. Specifically, the amount of CaO in the molten steel can be determined from the formula (3) below. In the formula (3), Ca is the amount [kg] of Ca added, y is the yield [%] of Ca, [S] is the concentration [% by mass] of S in the steel before addition of Ca, and W is the weight [kg] of the molten steel.

$$\{Ca \cdot y/100 - ([S] \cdot W/100) \cdot 40.08/32.07\}(56.08/40.08) \quad (3)$$

The yield y [%] of Ca is the ratio of Ca remaining in a tundish to the amount of Ca added and may be determined from past data. For example, before Ca is charged, the yield of Ca is computed for each of a prescribed number of previous charges, and the average of a set of the computed yield values for the respective charges is used as the yield of Ca. The prescribed number of previous charges before Ca is charged is preferably 10.

Examples of the method of obtaining the amount of $Al_2O_3$ in the molten steel may include: a method in which the amount of $Al_2O_3$ is approximated using T.[O] in the steel determined by a combustion analysis method; and a method of quantifying the amount of insol.Al using anomalous light emission behavior in spark discharge atomic emission spectroscopy. In the present invention, it is preferable to determine the amount of $Al_2O_3$ as an indicator directly correlating with the amount of $Al_2O_3$ using a method of quantifying the amount of alumina described later.

The present inventors examined the relation between the ratio of the amount of CaO to the amount of $Al_2O_3$ in the molten steel that are determined in the manners described above and the rate of occurrence of hydrogen induced cracking in an HIC resistance test. FIG. 1 is a graph showing the results. In FIG. 1, the vertical axis represents the rate (%) of occurrence of hydrogen induced cracking in the HIC resistance test, and the horizontal axis represents the amount of CaO/the amount of $Al_2O_3$ represented by the formula (4) below.

$$\frac{\{Ca \cdot y/100 - ([S] \cdot W/100) \cdot 40.08/32.07\}\frac{56.08}{40.08}}{([Al_2O_3] \cdot W/100)} \quad (4)$$

where Ca is the amount [kg] of Ca added,
y is an yield [%] of Ca,
[S] is a concentration [% by mass] of S in the steel before addition of Ca,
[$Al_2O_3$] is an amount [% by mass] of $Al_2O_3$ in the steel before addition of Ca, and
W is a weight [kg] of the molten steel.

As can be seen from FIG. 1, when the value of the formula (4) above is 0.5 or higher and 1.5 or lower, the rate of occurrence of hydrogen induced cracking in the HIC resistance test is low. A value of the above formula (4) of lower than 0.5 is not preferred because the amount of Ca is insufficient and S cannot be controlled with CaS. In this case, MnS is generated, causing deterioration of HIC resistance. A value of the above formula (4) of higher than 1.5 is not preferred because the amount of Ca is excessively large. In this case, the amount of inclusions becomes large, and a reduction in the melting point of the inclusions is not achieved, so that the HIC resistance deteriorates. Therefore, a preferred ratio of the amount of CaO to the amount of $Al_2O_3$ in the molten steel is represented by the formula (5) below.

$$0.5 \leq \frac{\{Ca \cdot y/100 - ([S] \cdot W/100) \cdot 40.08/32.07\}\frac{56.08}{40.08}}{([Al_2O_3] \cdot W/100)} \leq 1.5 \quad (5)$$

where Ca is the amount [kg] of Ca added,
y is an yield [%] of Ca,
[S] is a concentration [% by mass] of S in the steel before addition of Ca,
$[Al_2O_3]$ is an amount [% by mass] of $Al_2O_3$ in the steel before addition of Ca, and
W is a weight [kg] of the molten steel.

<Method of Quantifying the Amount of Alumina>

Part of aluminum (hereinafter referred to as Al) added to the molten steel in a steel refining step reacts with oxygen in the steel to form alumina ($Al_2O_3$), and the alumina gradually floats to the surface and is then removed from the molten steel. The rest of Al that is unreacted solidifies while remaining dissolved in the steel. After solidification of the steel, the alumina not removed by flotation remains in the steel in the form of alumina, and the unreacted Al is present in the steel mainly as solute Al. When a steel sample is dissolved by acid, the solute Al dissolves together with the steel, but the aluminum does not dissolve. Therefore, the solute Al and the alumina are separated from each other by acid dissolution. The former is referred to as acid-soluble Al (hereinafter referred to as sol.Al), and the latter is referred to as acid-insoluble Al (hereinafter referred to as insol.Al).

In a steel making process, spark discharge atomic emission spectroscopy has been widely used as a rapid analysis method for controlling the composition of steel. The spark discharge atomic emission spectroscopy has been used not only for component analysis but also as a method of quantifying the amount of oxide in steel for various cases. However, it has been difficult to precisely analyze a trace amount of alumina in steel, for example, 50 ppm or less, using this conventional analysis method.

In view of the above, the present inventors have reexamined the physicochemical meanings of the light emission intensity for each discharge pulse in a spark discharge light emission phenomenon and the distribution state of the light emission intensity and have found a method of quantifying the amount of alumina. Specifically, the present inventors used steel samples with equal sol.Al concentrations and different insol.Al concentrations (a sample with sol.Al=66 ppm and insol.Al=less than 10 ppm and a sample with sol.Al=66 ppm and insol.Al=32 ppm), and spark discharge was used to cause the samples to emit light. Then the present inventors observed the ratio of the intensity of light emission from Al to the intensity of light emission from iron (a value obtained by dividing the intensity of light emission from Al by the intensity of light emission from iron, this value is hereinafter referred to as Al/Fe intensity ratio) for each pulse over time.

The results showed many spike-like irregular points in the sample containing a larger amount of insol.Al. These spike-like points may be generated by discharge containing insol.Al nonuniformly present in the steel. The spark discharge is likely to concentrate on an inclusion (insol.Al). The observed Al intensity includes the intensity of light from sol.Al in the base iron and the intensity of light from an inclusion (insol.Al), and the ratio of them is different for each discharge pulse.

Figure 2:
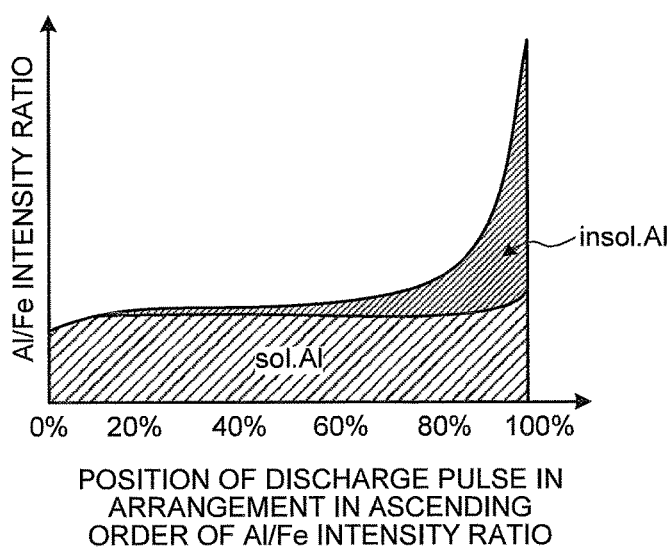
FIG. 2 is a conceptual diagram of the constituents of Al/Fe intensity ratios when the Al/Fe intensity ratios are arranged in order.

FIG. 2 is a conceptual diagram of the constituents of Al/Fe intensity ratios when the Al/Fe intensity ratios are arranged in order. The vertical axis represents the Al/Fe intensity ratio, and the horizontal axis represents the position (%) of each discharge pulse in an arrangement of discharge pulses sorted in ascending order of Al/Fe intensity ratio. As shown in FIG. 2, insol.Al is dominant on the side on which the Al/Fe intensity ratio is large, and sol.Al is dominant on the side on which the Al/Fe intensity ratio is small.

Since the sol.Al is uniformly present in the base iron, the value of the Al intensity originating from the sol.Al relative to the Fe intensity (the Al/Fe intensity ratio) should be constant even when the amount of base iron that evaporates upon discharge is changed. Specifically, the Al/Fe intensity ratio is the sum of a constant sol.Al intensity ratio and an indefinite insol.Al intensity ratio, and the magnitude of the Al/Fe intensity ratio is determined by the magnitude of the indefinite insol.Al intensity ratio. Therefore, the smaller the Al/Fe intensity ratio of a pulse is, the closer the Al/Fe intensity ratio to the sol.Al intensity ratio is. The amount of alumina can be quantified by subtracting the integrated intensity value associated with the sol.Al from the overall integrated value of the Al/Fe intensity ratio.

Specifically, the amount of alumina is quantified using the following procedure. First, the Al/Fe intensity ratio of aluminum to iron is determined for each of a plurality of discharge pulses (for example, 2,000 discharge pulses) (an intensity ratio computing step).

Next, an aluminum fraction determined using the formula (6) below is computed (an alumina fraction computing step).

Alumina fraction=Number of discharge pulses with Al/Fe intensity ratio larger than threshold value α/total number of discharge pulses (6)

Figure 3:
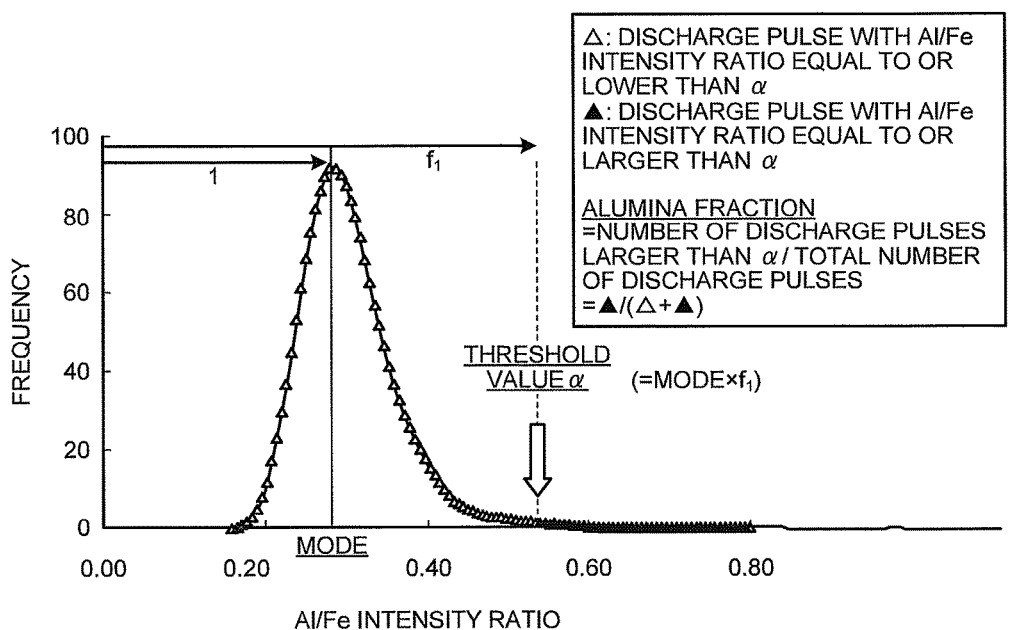
FIG. 3 is a frequency distribution diagram, in which the horizontal axis represents the Al/Fe intensity ratio for each discharge pulse and the vertical axis represents the frequency.

The threshold value α in the formula (6) above is specified as follows. As shown in FIG. 3, a frequency distribution diagram is produced, in which the horizontal axis represents the Al/Fe intensity ratio for each discharge pulse and the vertical axis represents the frequency. Then the threshold value α is specified as a value obtained by multiplying the mode of the Al/Fe intensity ratio determined from the frequency distribution diagram by a factor of $f_1$. Preferably, the value of $f_1$ is $1.5 \leq f_1 \leq 2.5$, as described later.

In the alumina fraction computing step, when the measurement is performed on samples treated by the same method, it is considered that the frequency distributions of the ratio of the intensity of light emission originating from the solute Al may have the same variation width, so long as the measurement is performed under the same measurement conditions. Therefore, by using a value obtained by multiplying the mode of the Al/Fe intensity ratio by a constant larger than 1 as the threshold value, it is considered that the ratio of the influence of the solute Al may be held constant, and this may allow the signal component originating from alumina to be separated. Accordingly, the number of discharge pulses in which the Al/Fe intensity ratio is larger than the value obtained by multiplying the mode by a factor of $f_1$ is determined, and a value obtained by dividing the determined number of discharge pulses by the total number of pulses is used as the alumina fraction. The $f_1$ value is within the range of 1.5 to 2.5 and more preferably within the range of 1.7 to 2.0. If the $f_1$ value is smaller than 1.5, the amount of data originating from the solute aluminum becomes large, and therefore the correlation with the amount of alumina deteriorates. If the $f_1$ value is larger than 2.5, the number of extracted discharge pulses containing signals originating from alumina becomes excessively small, and this causes an increase in variations of analysis.

Figure 4:
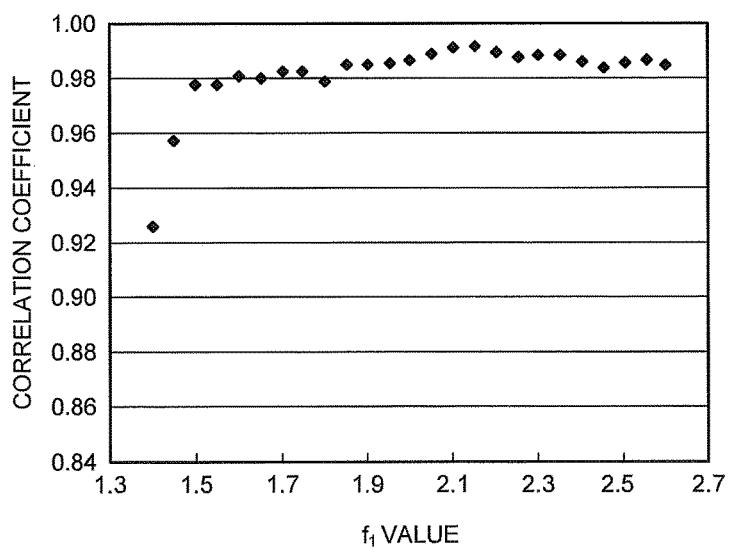
FIG. 4 is a graph showing the correlation between an alumina intensity ratio and the value of chemical analysis at each $f_1$ value.
Figure 5:
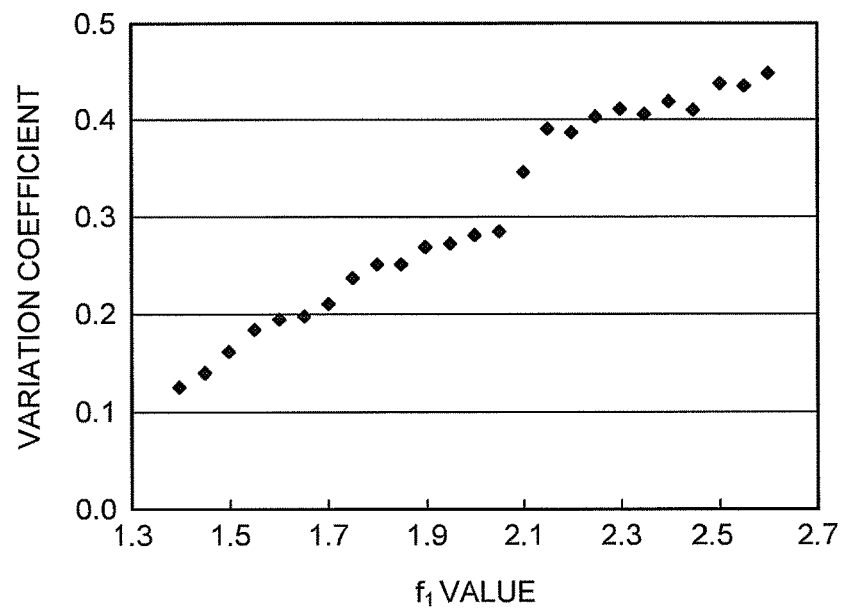
FIG. 5 is a graph showing the relation between the alumina intensity ratio and variations in repeated analysis at each $f_1$ value.

To examine the influence of the $f_1$ value when the alumina fraction is computed, the alumina intensity ratio (insol.Al intensity ratio) was computed at different $f_1$ values in the range of 1.4 to 2.6 at intervals of 0.05. FIG. 4 shows the correlation coefficient between the alumina intensity ratio and the value of chemical analysis at each $f_1$ value. FIG. 5 shows the coefficient of variation at each $f_1$ value in repeated analysis. As can be seen from FIG. 4, when $f_1$ becomes 1.5 or lower, the correlation coefficient between the alumina intensity ratio and the value of chemical analysis decreases abruptly. It is considered that this may be due to the influence of light emission originating from the solute aluminum. In addition, as can be seen from FIG. 5, as the $f_1$ value increases, the variations in the repeated analysis increase. This is because the number of extracted discharge pulses becomes excessively small. However, even when the $f_1$ takes values of 1.5 and 2.5, the standard deviation σd, which represents the accuracy of the analysis, takes values of 2.4 ppm and 1.9 ppm, respectively. Therefore, the analysis can be performed with higher precision than conventional methods.

Figure 6:
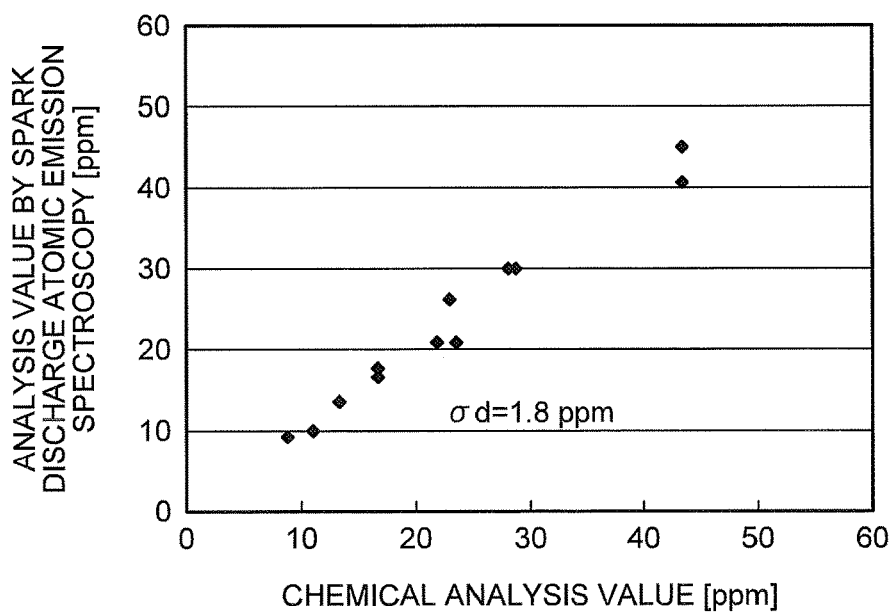
FIG. 6 is a graph showing the correlation between the concentration of alumina determined by the method of quantifying alumina according to an embodiment of the present invention at an $f_1$ value of 2.0 and a chemical analysis value.

FIG. 6 shows the correlation between the concentration of alumina determined by the method of quantifying the amount of alumina according to an embodiment of the present invention and the value of chemical analysis when the $f_1$ value is 2.0. The standard deviation σd, which represents the accuracy of the analysis, was 1.8 ppm.

Next, the Al/Fe intensity ratios of the discharge pulses obtained in the intensity computing step were sorted in ascending order, and the Al/Fe intensity ratio at a certain position was used as a representative aluminum intensity ratio.

Preferably, the representative aluminum intensity ratio in the arrangement of the Al/Fe intensity ratios of the respective discharge pulses in ascending order (see FIG. 2) is the intensity ratio at any position equal to or lower than 30% of the total number of discharge pulses arranged in ascending order. This is because, when the aluminum intensity ratio at a position larger than 30% of the total number of discharge pulses is used as the representative aluminum intensity ratio, the influence of the amount of alumina present in the sample becomes too large. In this case, the value used is not the representative value for dividing the acid-soluble Al (sol.Al) from alumina with high precision, so that the precision of the analysis deteriorates.

Next, the alumina intensity ratio is computed using the product of the alumina fraction obtained in the alumina fraction computing step and the representative aluminum intensity ratio.

In this manner, the amount of alumina (in the steel), which is the object of the analysis, is rapidly quantified using the alumina intensity ratio determined by the spark discharge atomic emission spectroscopy and a calibration curve prepared in advance using true values determined by the chemical analysis method.

The same Ca-added steel materials as above were used for the samples for the calibration curve. For each sample, the coefficients were set using the Al/Fe intensity ratios obtained in advance by the spark discharge atomic emission spectroscopy, and then the curve of correlation between the computed alumina intensity ratio and the true value was used as the calibration curve.

The amount of alumina in molten steel is easily changed over time by contact with air etc. Therefore, preferably, the spark discharge atomic emission spectrophotometer is placed at a position as close as possible to the production site. If possible, on-site analysis at the production apparatus is most preferred.

It was found from the examination that the amount of S in steel was almost unchanged in steps after the AP treatment. Specifically, the analysis can be performed between completion of the AP treatment and addition of Ca without any difficulty, and, for example, a combustion method, which is a high precision method of analyzing S in steel, can be well applied.

As described above, according to the method of producing a steel material in this embodiment, the molten steel components can be controlled at an inclusion composition that allows a reduction in the occurrence of hydrogen induced cracking. Therefore, the optimization of the amount of Ca added to the molten steel can be achieved, and a steel material having high HIC resistance can thereby be produced.

The above embodiment is merely an example for implementing the present invention, and the present invention is not limited thereto. Various modifications according to specifications etc. are within the scope of the present invention, and it is obvious from the above description that various other embodiments within the scope of the present invention are possible.

EXAMPLES

The advantageous effects of the present invention were confirmed in Examples described below.

Oxygen was blown into molten steel of about 250 ton in a converter, and then the molten steel was discharged into a ladle and conveyed to an RH vacuum degassing apparatus. In the RH vacuum degassing apparatus, refining such as component adjustment was performed, and a prescribed amount of an Al alloy was added to perform deoxidization treatment. After the addition of the Al alloy, a molten steel sample was collected, and a spark discharge atomic emission spectrophotometer provided to the apparatus was used to analyze the amount of $Al_2O_3$. Then, as one of Inventive Examples 1 to 5 shown in TABLE 1, a CaSi wire with a Ca fineness of 30% was added such that $CaO/Al_2O_3$ satisfied the amount of Ca in the above formula (5).

Ca was quantified using general analysis means, and a quantified value computed using the above-described method of quantifying the amount of alumina was used as the amount of $Al_2O_3$. The same Ca-added steel materials as those described above were used for the samples for the calibration curve. For each sample, the coefficients were set using the Al/Fe intensity ratios obtained in advance by the spark discharge atomic emission spectroscopy, and then the curve of correlation between the computed alumina intensity ratio and the amount of alumina determined by chemical analysis was used as the calibration curve.

In Comparative Examples 1 to 3 shown in TABLE 1, Ca was added in such an amount that $CaO/Al_2O_3$ had an inclusion composition outside the range of the above formula (5).

TABLE 1

|  | Amount of CaSi added [kg] | Amount of Ca in CaSi [kg] | Amount of Al$_2$O$_3$ in molten steel after completion of RH [%] | Yield of Ca [%] | [S] after completion of RH [%] | Weight of molten steel [ton] | Value of formula (4) | Formula (5) |
|---|---|---|---|---|---|---|---|---|
| Inventive example 1 | 65 | 19.5 | 0.0010 | 20 | 0.00060 | 250 | 1.1 | ○ |
| Inventive example 2 | 50 | 15 | 0.0008 | 20 | 0.00050 | 250 | 1.0 | ○ |
| Inventive example 3 | 65 | 19.5 | 0.0015 | 20 | 0.00040 | 250 | 1.0 | ○ |
| Inventive example 4 | 52 | 15.6 | 0.0012 | 20 | 0.00060 | 250 | 0.6 | ○ |
| Inventive example 5 | 50 | 15 | 0.0010 | 20 | 0.00030 | 250 | 1.2 | ○ |
| Inventive example 1 | 82 | 24 | 0.0010 | 20 | 0.00030 | 250 | 2.2 | X |
| Inventive example 2 | 70 | 21 | 0.0009 | 20 | 0.00040 | 250 | 1.8 | X |
| Inventive example 3 | 5 | 13.5 | 0.0015 | 20 | 0.00050 | 250 | 0.4 | X |

Figure 7:
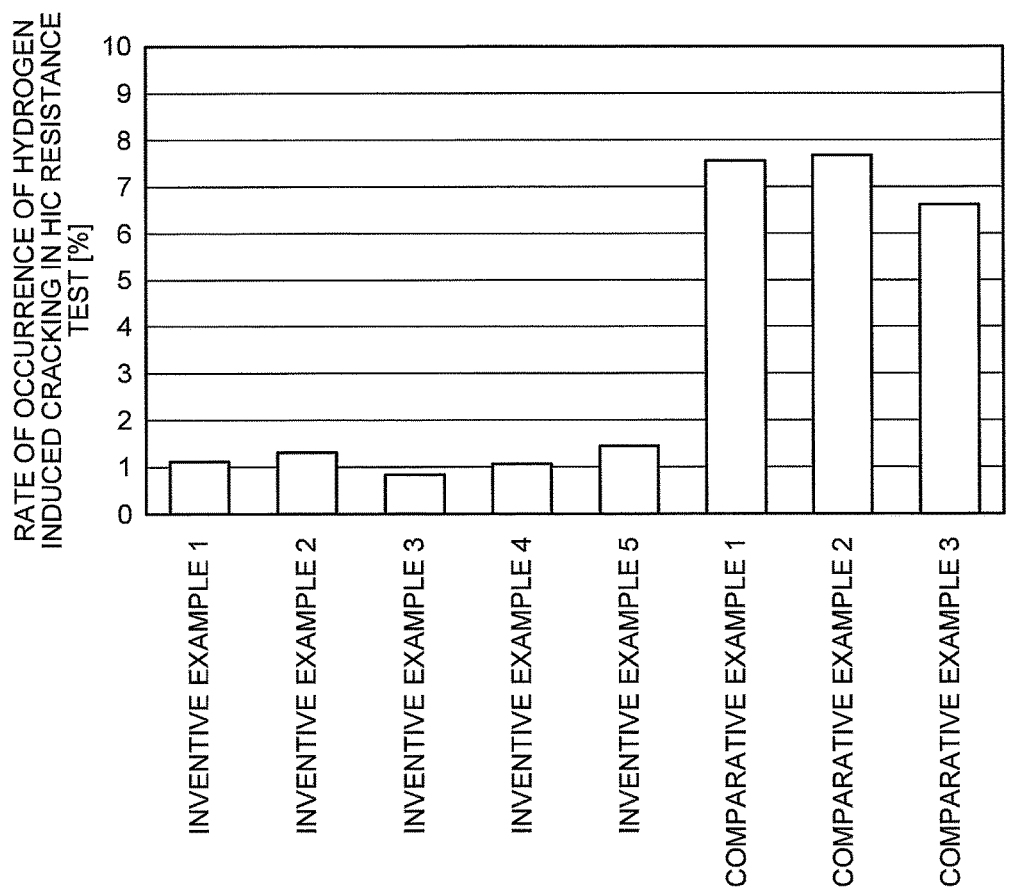
FIG. 7 is a graph showing the results of experiments in Examples in which the rate of occurrence of hydrogen induced cracking in the HIC resistance test was compared among Inventive Examples and Comparative Examples.

After Ca was added under the conditions in one of Inventive Examples 1 to 5 and Comparative Examples 1 to 3 shown in TABLE 1, casting was performed. Then test samples were cut from some positions in the slab, and an HIC resistance test was performed. FIG. 7 shows the rate of occurrence of hydrogen induced cracking. As shown in FIG. 7, the rate of occurrence of hydrogen induced cracking in the HIC test was 6.5% or higher in the Comparative Examples. However, in the Inventive Examples, the rate of occurrence of hydrogen induced cracking was 1.5% or lower. It was found from these results that, when the amount of Ca added is within the range suggested by the present invention, the rate of occurrence of hydrogen induced cracking in the HIC resistance test can be significantly reduced.

The present invention can be applied to treatment for controlling the components of molten steel contained in a container by adding Ca to the molten steel in order to produce a steel material having high HIC resistance.

The invention claimed is:

1. A method of producing a steel material, the method comprising a step of adding Ca to molten steel with an amount of Ca adjusted within a range satisfying the formula (1) below:

$$0.5 \leq \frac{\{Ca \cdot y/100 - ([S] \cdot W/100) \cdot 40.08/32.07\} \frac{56.08}{40.08}}{([Al_2O_3] \cdot W/100)} \leq 1.5 \quad (1)$$

where Ca is the amount [kg] of Ca added,
y is an yield [%] of Ca,
[S] is a concentration [% by mass] of S in the steel before addition of Ca,
[Al$_2$O$_3$] is an amount [% by mass] of Al$_2$O$_3$ in the steel before addition of Ca, and
W is a weight [kg] of the molten steel.

2. The method of producing a steel material according to claim 1, further comprising a step of analyzing, after secondary refining, the amount of Al$_2$O$_3$ in the molten steel, and thereafter adding CaSi to the molten steel in a ladle.

3. The method of producing a steel material according to claim 1, the method producing the steel material with the amount of Al$_2$O$_3$ in the molten steel analyzed by spark discharge atomic emission spectroscopy, the method further comprising an intensity ratio computing step of determining aluminum/iron light emission intensity ratios of a plurality of discharge pulses, an alumina fraction computing step of computing an alumina fraction determined using the formula (2) below, a step of arranging the light emission intensity ratios of the respective discharge pulses obtained in the intensity ratio computing step in ascending order, using a light emission intensity ratio at a certain position equal to or lower than 30% of the total number of discharge pulses as a representative aluminum intensity ratio, and then computing an alumina intensity ratio (=the alumina fraction×a representative aluminum intensity ratio) using a product of the alumina fraction computed in the alumina fraction computing step and the representative aluminum intensity ratio, and a quantitative step of computing the amount of alumina (in the steel) using a relational formula between the alumina intensity ratio and the amount of alumina (in the steel) determined by chemical analysis:

Alumina fraction=Number of discharge pulses with Al/Fe intensity ratio larger than threshold value α/total number of pulses   (2)

where the threshold value α is determined using a frequency distribution diagram having a horizontal axis representing the light emission intensity ratios for the discharge pulses and a vertical axis representing frequency, the threshold value α being a value obtained by multiplying a mode of the light emission intensity ratios by a factor of $f_1$ ($1.5 \leq f_1 \leq 2.5$).

4. The method of producing a steel material according to claim 2, the method producing the steel material with the amount of Al$_2$O$_3$ in the molten steel analyzed by spark discharge atomic emission spectroscopy, the method further comprising an intensity ratio computing step of determining aluminum/iron light emission intensity ratios of a plurality of discharge pulses, an alumina fraction computing step of computing an alumina fraction determined using the formula (2) below, a step of arranging the light emission intensity ratios of the respective discharge pulses obtained in the intensity ratio computing step in ascending order, using a light emission intensity ratio at a certain position equal to or lower than 30% of the total number of discharge pulses as a representative aluminum intensity ratio, and then computing an alumina intensity ratio (=the alumina fraction×a representative aluminum intensity ratio) using a product of the alumina fraction computed in the alumina fraction computing step and the representative aluminum intensity ratio, and a quantitative step of computing the amount of alumina (in the steel) using a relational formula between the alumina intensity ratio and the amount of alumina (in the steel) determined by chemical analysis:

$$\text{Alumina fraction} = \text{Number of discharge pulses with Al/Fe intensity ratio larger than threshold value } \alpha/\text{total number of pulses} \quad (2)$$

where the threshold value $\alpha$ is determined using a frequency distribution diagram having a horizontal axis representing the light emission intensity ratios for the discharge pulses and a vertical axis representing frequency, the threshold value $\alpha$ being a value obtained by multiplying a mode of the light emission intensity ratios by a factor of $f_1 (1.5 \leq f_1 \leq 2.5)$.

* * * * *